United States Patent [19]

Gehrer et al.

[11] Patent Number: 5,866,733
[45] Date of Patent: Feb. 2, 1999

[54] PREPARATION OF DIARYLETHANES

[75] Inventors: Eugen Gehrer, Ludwigshafen; Klemens Massonne, Westheim; Wolfgang Harder, Weinheim, all of Germany

[73] Assignee: BASF Aktiengesellschaft, Ludwigshafen, Germany

[21] Appl. No.: 679,666

[22] Filed: Jul. 12, 1996

[51] Int. Cl.⁶ .............................. C07C 15/12; C07C 2/02
[52] U.S. Cl. .................. 585/25; 585/20; 585/21; 585/23; 585/24; 585/422; 585/426
[58] Field of Search .................. 585/25, 20, 21, 585/23, 24, 422, 426

[56] References Cited

U.S. PATENT DOCUMENTS

| | | | |
|---|---|---|---|
| 4,289,918 | 9/1981 | Sato et al. | 585/422 |
| 4,329,529 | 5/1982 | Nambu | 585/20 |
| 4,493,943 | 1/1985 | Sato et al. | 585/25 |
| 4,689,436 | 8/1987 | Minokani et al. | 585/422 |

FOREIGN PATENT DOCUMENTS

| | | |
|---|---|---|
| 317907 | 5/1989 | European Pat. Off. . |
| 1281757 | 5/1962 | France . |
| 2021637 | 12/1979 | United Kingdom . |
| 1579815 | 11/1980 | United Kingdom . |

*Primary Examiner*—Elizabeth D. Wood
*Attorney, Agent, or Firm*—Keil & Weinkauf

[57] ABSTRACT

Diarylethanes of the formula I

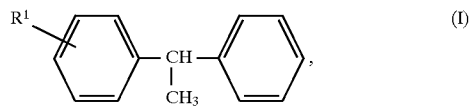

where $R^1$ is hydrogen or $C_1$–$C_8$-alkyl, are prepared by reacting benzene with a styrene of the formula III

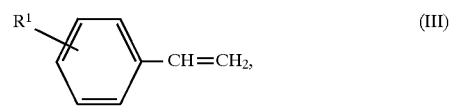

where $R^1$ has the abovementioned meanings, by a process in which the reaction is carried out batchwise or continuously in the liquid or supercritical phase at from 150° to 350° C. and from 5 to 200 bar in the presence of a strongly acidic large-pore zeolite.

15 Claims, No Drawings

PREPARATION OF DIARYLETHANES

BACKGROUND OF THE INVENTION

1. Field of the Invention

The present invention relates to a process for the preparation of diarylethanes by reacting an aromatic with styrene in the presence of an acid heterogeneous catalyst at elevated temperatures and superatmospheric pressures.

2. Description of the Related Art

The preparation of diphenylethane by reacting an aromatic with styrene or with a styrene derivative is described in JP63-238028 (1988), where Y zeolites are used, in Polymer Journal 12 No. 6 (1980), 407, where Nafion, Amberlyst 15 or $CF_3SO_3H$ is used, and in EP-A-421 340, where L zeolites are used. The syntheses described give usable yields only with the use of alkylated aromatics, but these yields are unsatisfactory. When the aromatic used is benzene, oligomers of styrene are predominantly formed.

It is an object of the present invention to remedy the abovementioned disadvantages.

SUMMARY OF THE INVENTION

We have found that this object is achieved by a novel and improved process for the preparation of diarylethanes of the general formula I

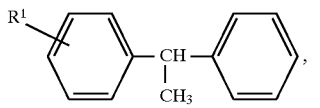

where $R^1$ is hydrogen or $C_1$-$C_8$-alkyl, by reacting benzene with a styrene of the general formula III

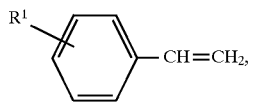

where $R^1$ has the abovementioned meanings, wherein the reaction is carried out batchwise or continuously in the liquid or supercritical phase at from 150° to 350° C. and from 5 to 200 bar in the presence of an acidic heterogeneous catalyst.

DESCRIPTION OF THE PREFERRED EMBODIMENTS

The novel process can be carried out as follows:

The reaction of the aromatic II with the styrene III can be carried out batchwise or, preferably, continuously in a pressure-resistant apparatus, such as an autoclave, in the liquid or supercritical phase at from 150° to 350° C., preferably from 180° to 230° C., particularly preferably from 190° to 220° C., and from 5 to 200, preferably from 10 to 130, bar, particularly preferably under autogenous pressure or by increasing the pressure by starting from 1 to 50 bar, in the presence of an acidic heterogeneous catalyst. The pressure must therefore be sufficiently high for the system to remain liquid or, if required, in the supercritical phase under the reaction conditions.

The novel process can be carried out, for example, in a continuously stirred reactor or a fixed-bed reactor.

In the case of the reaction in a fixed-bed reactor, the acidic heterogeneous catalyst is as a rule initially taken in the form of moldings in the fixed-bed reactor, and the reaction mixture is passed several times through this fixed bed with vigorous backmixing, fresh solution of starting materials being metered continuously into the circulation and an equivalent amount of production solution being removed continuously.

Suitable acidic heterogeneous catalysts are, as a rule, strongly acidic, large-pore zeolites, such as 12-ring zeolites of the beta-zeolite (BEA), HY zeolite or mordenite type. As a rule, the catalyst may be used either in powder form suspended in the reaction system or as moldings in a fixed-bed reactor.

Beta-zeolites are disclosed, for example, in U.S. Pat. No. 3,308,069. They can be crystallized by means of tetraethylammonium hydroxide at from 100° to 150° C. from gels having the composition $TEA_2O:SiO_2:Al_2O_3:Na_2O:H_2O$, where the $SiO_2/Al_2O_3$ ratio may be from 10:1 to 200:1, the $Na_2O/TEAOH$ ratio from 0 to 1:1, the $TEAOH/SiO_2$ ratio from 0.1:1 to 1:1 and the $H_2O/TEAOH$ ratio from 20:1 to 75:1. They have a three-dimensional pore system possessing large pores and 12-membered rings with diameters of 6.5× 5.6 and 7.5×5.7 Å.

As a rule, the reaction is preferably carried out under conditions which permit only a low concentration of styrene. This can be achieved by the use of dilute styrene solutions or by slow metering of the styrene into the reaction system. A particularly preferred method for the batchwise preparation comprises initially taking the aromatic together with the catalyst suspended therein in a stirred kettle and adding the styrene (or a styrene solution) dropwise during the reaction sufficiently slowly that a flow equilibrium is established between the metered and the reacted styrene at a low concentration level. The steady-state concentration of styrene should not exceed 3%, preferably 0.1%, particularly preferably 0.05%.

The diphenylethanes I can be obtained via the bottom of a distillation column.

$R^1$ in the compounds I and III has the following meaning and may be in ortho-, meta- or para-position.

hydrogen or $C_1$-$C_8$-alkyl, preferably $C_1$-$C_4$-alkyl, such as methyl, ethyl, n-propyl, isopropyl, n-butyl, isobutyl, sec-butyl or tert-butyl, particularly preferably methyl or ethyl.

The compounds I and III in which $R^1$ is hydrogen, eg. 1,1-diphenylethane and styrene, are particularly preferred.

Diphenylethane is an important intermediate for the preparation of diphenylethene, which is used as comonomer for the preparation of plastics. Diphenylethene can be obtained in good yields by catalytic dehydrogenation of diphenylethane.

EXAMPLES

A gas chromatograph having a 30 m capillary column (DB5, 0.1 μm) was used for the analysis of the experiments below. (Temperature program: 5 minutes at 60° C., 10° C./minute to 300° C., 15 minutes at final temperature). The quantification was carried out with the aid of toluene as internal standard.

The three dimers formed (identified by means of GC/MS) were counted together in the list below. Their calibration factor was set equal to that for diphenylethane. The calibration factors for benzene (not listed), styrene and diphenylethane were determined by means of a concentration series with toluene as internal standard.

Catalyst A 100 g of β-zeolite powder (ZEOCAT® BETA from Uetikon; $SiO_2$=91%, $Al_2O_3$=7.8%, $Na_2O$=0.5%, $K_2O$=

0.7%) were stirred with 1 liter of 20% strength NH$_4$Cl solution for 2 hours at 80° C., decanted, washed with 3 times 500 ml of water, dried at 110° C. for 16 hours and calcined at 500° C. for 3 hours.

Example 1

2 g of catalyst A were initially taken together with 30 g of benzene in a 50 ml pressure-resistant glass vessel, and a mixture of 10% of styrene and 90% of benzene was metered in at a rate of 10 ml/h while stirring.

A calming zone in the form of a 20 cm long pressure-resistant glass tube (diameter 1 cm) in which the catalyst could settle out was installed above the pressure-resistant glass vessel. The internal pressure of the vessel was kept at 15 bar by means of an overflow valve. The temperature of the pressure-resistant glass autoclave was brought to 200° C. The discharge product was analyzed by means of GC, and the results are summarized in Table 1.

TABLE 1

| Time on stream [h] | Styrene [%] | 1,1-Diphenyl-ethane | Conversion [%] | Yield [%] |
|---|---|---|---|---|
| 6 | 0.2 | 7.08 | 98 | — |
| 22 | 0.13 | 12.7 | 98.7 | 72.6 |
| 90 | 0.06 | 16.7 | 99.4 | 95.4 |
| 150 | 0.05 | 13.5 | 99.5 | 76.9 |
| 200 | 0.03 | 14.2 | 99.7 | 81.3 |
| 310 | 0.03 | 16.9 | 99.7 | 96.6 |

Example 2

An experiment similar to Example 1 was carried out with the addition of 0.1% of tert-butylpyrocatechol as stabilizer. The results are summarized in Table 2.

TABLE 2

| Time on stream [h] | Styrene [%] | 1,1-Diphenyl-ethane | Conversion [%] | Yield [%] |
|---|---|---|---|---|
| 5 | 0.02 | 3.45 | 99.8 | — |
| 21 | <0.02 | 12.0 | 100 | 68.6 |
| 101 | 0.04 | 17.3 | 99.6 | 98.8 |
| 149 | 0.2 | 17.4 | 98 | 98.9 |
| 197 | 1.17 | 14.8 | 88 | 84.4 |

Example 3

10 g of catalyst and 100 g of benzene were initially taken in a 250 ml three-necked flask, similarly to Example 1. After heating up to 80° C. at atmospheric pressure, a mixture of 10% of styrene and 90% of benzene was metered in at a rate of 10 ml/h. Rapid deactivation occurred under these conditions. The results are summarized in Table 3.

TABLE 3

| Time on stream [h] | Styrene [%] | 1,1-Diphenyl-ethane | Conversion [%] | Yield [%] |
|---|---|---|---|---|
| 6 | <0.01 | 2.86 | 100 | — |
| 22 | <0.01 | 13.5 | 100 | 77.0 |
| 26 | 0.06 | 17.3 | 99.4 | 98.8 |
| 30 | 0.28 | 13.7 | 97.2 | 78.2 |

TABLE 3-continued

| Time on stream [h] | Styrene [%] | 1,1-Diphenyl-ethane | Conversion [%] | Yield [%] |
|---|---|---|---|---|
| 38 | 1.04 | 9.5 | 89.6 | 54.3 |
| 54 | 4.14 | 3.24 | 58.6 | 18.5 |
| 90 | 8.74 | 0.34 | 12.6 | 1.9 |

Catalyst B 220 g of β-zeolite powder (ZEOCAT® BETA from Uetikon; SiO$_2$=91%, Al$_2$O$_3$=7.8%, Na$_2$O=0.5%, K$_2$O=0.7%) were compacted with 5% of Walocel® and 230 g of water for 45 minutes in a kneader. The material was then molded at 70 bar to give 2 mm extrudates, which were dried at 110° C. and calcined at 500° C. for 16 hours.

195 g of these extrudates were subjected to ion exchange with 3 liters of 20% strength NH$_4$Cl solution at 80° C. for 2 hours and washed with 10 liters of water. Thereafter, a second ion exchange was carried out, likewise with 3 liters of 20% strength NH$_4$Cl solution at 80° C. for 2 hours, and the product was then washed chlorine-free, dried at 110° C. and calcined for 5 hours at 500° C.

Example 4

10 g of β-zeolite extrudates (catalyst B) were initially taken in a catalyst basket in a 50 ml steel autoclave. The autoclave was filled with 30 ml of benzene and heated to 250° C. with stirring, and a mixture of 10% of styrene and 90% of benzene was metered in continuously. The product mixture was removed continuously via an overflow valve. The overflow valve kept the pressure at 50 bar. The discharge products were analyzed by means of GC. The results are summarized in Table 4.

TABLE 4

| Time on stream [h] | Temp. [°C.] | Loading [g/h] | Styrene [%] | Diphenyl-ethane [%] | Conversion [%] | Yield [%] |
|---|---|---|---|---|---|---|
| 24 | 250 | 50 | 0.02 | 8.3 | 99.8 | 47 |
| 48 | 230 | 50 | 0.03 | 12.7 | 99.7 | 72.6 |
| 72 | 230 | 50 | 0.03 | 14.7 | 99.7 | 84 |
| 96 | 230 | 50 | 0.03 | 13.5 | 99.7 | 77.3 |
| 120 | 230 | 50 | 0.04 | 14.1 | 99.6 | 80.6 |
| 144 | 230 | 50 | 0.04 | 14.2 | 99.6 | 81.1 |
| 168 | 230 | 100 | 0.09 | 14.7 | 99.1 | 84 |
| 192 | 230 | 200 | 0.14 | 15.8 | 98.6 | 90.2 |
| 212 | 230 | 200 | 1.78 | 11.1 | 82.2 | 63.4 |

We claim:
1. A process for the preparation of a diarylethane of the formula I

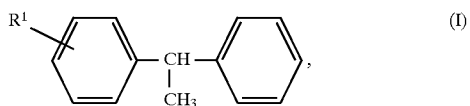

where R$^1$ is hydrogen or C$_1$-C$_8$-alkyl, by reacting benzene with a styrene of the formula III

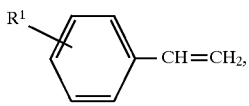

where $R^1$ has the abovementioned meanings, wherein the reaction is carried out batchwise or continuously at from 150° to 350° C. and from 5 to 200 bar in the presence of a acidic large-pore zeolite and wherein the pressure is sufficiently high for the system to remain in the liquid or supercritical phase.

2. The process of claim 1, wherein the zeolite is a large-pore 12-ring zeolite.

3. The process of claim 1, wherein the zeolite is a beta-zeolite, an HY zeolite or a mordenite.

4. The process of claim 1, wherein $R^1$ is hydrogen.

5. The process of claim 1, wherein the reaction is carried out at from 180° to 230° C.

6. The process of claim 1, wherein the reaction is carried out at from 10 to 130 bar.

7. The process of claim 1, wherein the reaction is carried out under autogeneous pressure or by increasing the pressure by from 1 to 50 bar.

8. The process of claim 1, wherein the styrene concentration in the reaction system is not more than 3%.

9. The process of claim 1, wherein the styrene concentration in the reaction system is not more than 0.1%.

10. The process of claim 1, wherein the styrene concentration in the reaction system is not more than 0.05%.

11. The process of claim 1, wherein the reaction is carried out in a continuously mixed reactor or in a fixed-bed reactor.

12. The process of claim 1, wherein the zeolite is a beta-zeolite or a mordenite.

13. The process of claim 1, which is carried out in a fixed bed reactor and which further comprises a) repeatedly circulating the reaction mixture through the fixed bed reactor with vigorous backmixing, b) continuously metering into the circulated reaction mixture a solution of the starting materials, and c) continuously removing from the circulated reaction mixture an amount equivalent to the amount of the added solution of the starting material.

14. The process of claim 1, which is carried out at from 180° C. to 230° C.

15. The process of claim 1, which is carried out at from 190° C. to 220° C.

* * * * *